(12) United States Patent
Kaduchak et al.

(10) Patent No.: US 8,714,014 B2
(45) Date of Patent: May 6, 2014

(54) SYSTEM AND METHOD FOR ACOUSTIC FOCUSING HARDWARE AND IMPLEMENTATIONS

(75) Inventors: Gregory Kaduchak, Los Alamos, NM (US); Michael D. Ward, Los Alamos, NM (US)

(73) Assignee: Life Technologies Corporation, Carlsbad, CA (US)

( * ) Notice: Subject to any disclaimer, the term of this patent is extended or adjusted under 35 U.S.C. 154(b) by 1197 days.

(21) Appl. No.: 12/209,084

(22) Filed: Sep. 11, 2008

(65) Prior Publication Data

US 2009/0178716 A1    Jul. 16, 2009

Related U.S. Application Data

(60) Provisional application No. 61/021,443, filed on Jan. 16, 2008.

(51) Int. Cl.
*G01H 17/00* (2006.01)
*H01L 41/04* (2006.01)

(52) U.S. Cl.
USPC .......................................... 73/570.5; 310/367

(58) Field of Classification Search
USPC .................. 73/570.5; 310/367, 368, 369, 370
See application file for complete search history.

(56) References Cited

U.S. PATENT DOCUMENTS

| | | | |
|---|---|---|---|
| 2,900,536 A * | 8/1959 | Palo | 310/330 |
| 3,882,732 A | 5/1975 | Fletcher et al. | |
| 4,055,491 A | 10/1977 | Porath-Furedi | |
| 4,265,124 A | 5/1981 | Lim et al. | |
| 4,285,810 A | 8/1981 | Kirkland et al. | |
| 4,350,683 A | 9/1982 | Galfre et al. | |
| 4,434,230 A | 2/1984 | Ritts, Jr. | |
| 4,492,752 A | 1/1985 | Hoffman et al. | |
| 4,523,682 A | 6/1985 | Barmatz et al. | |
| 4,523,982 A | 6/1985 | Lee | |
| 4,604,542 A | 8/1986 | Thompson | |

(Continued)

FOREIGN PATENT DOCUMENTS

| | | |
|---|---|---|
| CN | 1524948 | 9/2004 |
| CN | 101060898 | 10/2007 |

(Continued)

OTHER PUBLICATIONS

Aleksandrov et al., "Pulsed laser fluorescence spectrometer," translation from Zhurnal Prikladnoi Spektroskopii, 47:686-692 (1987).

(Continued)

*Primary Examiner* — Peter Macchiarolo
*Assistant Examiner* — Rose M Miller

(57) ABSTRACT

An acoustic focusing capillary includes a capillary coupled to at least one vibration source possessing a groove. A method of manufacturing such an acoustic focusing capillary includes providing a capillary and a vibration source, machining a groove into the vibration source, and coupling the vibration source to the capillary at the groove. Another method relates to focusing a particle stream and includes flowing a sheath fluid into an outer confine of a capillary, flowing a particle stream into a central core of the capillary, and acoustically focusing the particle stream by applying acoustic radiation pressure to the particle stream at a first location along the capillary. The particle stream may be further focused by hydrodynamically focusing it at a second location along the capillary downstream of the first location.

6 Claims, 10 Drawing Sheets

(56) References Cited

U.S. PATENT DOCUMENTS

| | | | |
|---|---|---|---|
| 4,673,512 A | 6/1987 | Schram |
| 4,743,361 A | 5/1988 | Schram |
| 4,743,631 A | 5/1988 | Greco et al. |
| 4,759,775 A | 7/1988 | Peterson et al. |
| 4,777,823 A | 10/1988 | Barmatz et al. |
| 4,845,025 A | 7/1989 | Lary et al. |
| 4,867,559 A | 9/1989 | Bach |
| 4,877,516 A | 10/1989 | Schram |
| 4,913,883 A | 4/1990 | Imai et al. |
| 4,964,303 A | 10/1990 | Barmatz et al. |
| 4,979,824 A | 12/1990 | Mathies et al. |
| 4,987,086 A | 1/1991 | Brosnan et al. |
| 4,991,923 A | 2/1991 | Kino et al. |
| 5,006,266 A | 4/1991 | Schram |
| 5,030,002 A | 7/1991 | North, Jr. |
| 5,032,381 A | 7/1991 | Bronstein et al. |
| 5,040,890 A | 8/1991 | North, Jr. |
| 5,079,959 A | 1/1992 | Miyake et al. |
| 5,085,783 A | 2/1992 | Feke et al. |
| 5,164,094 A | 11/1992 | Stuckart |
| 5,225,089 A | 7/1993 | Benes et al. |
| 5,346,670 A | 9/1994 | Renzoni et al. |
| 5,376,551 A | 12/1994 | Yoshikami |
| 5,395,588 A | 3/1995 | North, Jr. et al. |
| 5,430,541 A | 7/1995 | Sapp et al. |
| 5,491,344 A | 2/1996 | Kenny et al. |
| 5,504,337 A | 4/1996 | Lakowicz et al. |
| 5,527,460 A | 6/1996 | Trampler et al. |
| 5,528,045 A | 6/1996 | Hoffman et al. |
| 5,547,849 A | 8/1996 | Baer et al. |
| 5,626,767 A | 5/1997 | Trampler et al. |
| 5,644,388 A | 7/1997 | Maekawa et al. |
| 5,674,698 A | 10/1997 | Zarling et al. |
| 5,688,406 A | 11/1997 | Dickinson et al. |
| 5,711,888 A | 1/1998 | Trampler et al. |
| 5,739,902 A | 4/1998 | Gjelsnes et al. |
| 5,798,222 A | 8/1998 | Goix |
| 5,800,861 A | 9/1998 | Chiang et al. |
| 5,831,166 A | 11/1998 | Kozuka et al. |
| 5,981,180 A | 11/1999 | Chandler et al. |
| 6,003,388 A | 12/1999 | Oeftering |
| 6,055,859 A | 5/2000 | Kozuka et al. |
| 6,074,879 A | 6/2000 | Zelmanovic et al. |
| 6,090,295 A | 7/2000 | Raghavarao et al. |
| 6,197,593 B1 | 3/2001 | Deka et al. |
| 6,216,538 B1 | 4/2001 | Yasuda et al. |
| 6,221,258 B1 | 4/2001 | Feke et al. |
| 6,248,590 B1 | 6/2001 | Malachowski et al. |
| 6,255,118 B1 | 7/2001 | Alfano et al. |
| 6,309,886 B1 | 10/2001 | Ambrose et al. |
| 6,332,541 B1 | 12/2001 | Coakley et al. |
| 6,348,687 B1 | 2/2002 | Brockmann et al. |
| 6,373,567 B1 | 4/2002 | Wise et al. |
| 6,449,563 B1 | 9/2002 | Dukhin et al. |
| 6,467,350 B1 | 10/2002 | Kaduchak et al. |
| 6,549,275 B1 | 4/2003 | Cabuz et al. |
| 6,565,727 B1 | 5/2003 | Shenderov et al. |
| 6,592,821 B1 | 7/2003 | Wada et al. |
| 6,644,118 B2 | 11/2003 | Kaduchak et al. |
| 6,647,739 B1 | 11/2003 | Kim |
| 6,668,664 B1 * | 12/2003 | Ohkawa ................. 73/861.27 |
| 6,683,314 B2 | 1/2004 | Oostman, Jr. et al. |
| 6,713,019 B2 | 3/2004 | Ozasa et al. |
| 6,773,556 B1 | 8/2004 | Brockie et al. |
| 6,797,158 B2 | 9/2004 | Feke et al. |
| 6,813,017 B1 | 11/2004 | Hoffman et al. |
| 6,816,257 B2 | 11/2004 | Goix |
| 6,831,279 B2 | 12/2004 | Ho |
| 6,881,314 B1 | 4/2005 | Wang et al. |
| 7,008,540 B1 | 3/2006 | Weavers et al. |
| 7,018,819 B2 | 3/2006 | Orwar et al. |
| 7,052,864 B2 | 5/2006 | Durkop et al. |
| 7,081,192 B1 | 7/2006 | Wang et al. |
| 7,108,137 B2 | 9/2006 | Lal et al. |
| 7,113,266 B1 | 9/2006 | Wells |
| 7,161,665 B2 | 1/2007 | Johnson |
| 7,255,780 B2 | 8/2007 | Shenderov |
| 7,262,838 B2 | 8/2007 | Fritz |
| 7,315,357 B2 | 1/2008 | Ortyn et al. |
| 7,329,545 B2 | 2/2008 | Pamula et al. |
| 7,340,957 B2 | 3/2008 | Kaduchak et al. |
| 7,362,432 B2 | 4/2008 | Roth |
| 7,373,805 B2 | 5/2008 | Hawkes |
| 7,403,125 B2 | 7/2008 | Rich |
| 7,477,363 B2 | 1/2009 | Nagai |
| 7,570,676 B2 | 8/2009 | Essaian et al. |
| 7,837,040 B2 | 11/2010 | Ward et al. |
| 2002/0121285 A1 | 9/2002 | Poniatowski et al. |
| 2002/0129669 A1 | 9/2002 | Buchanan et al. |
| 2002/0162393 A1 | 11/2002 | Kaduchak et al. |
| 2003/0098421 A1 | 5/2003 | Ho |
| 2004/0057866 A1 | 3/2004 | Zumeris et al. |
| 2004/0065599 A1 | 4/2004 | Lal et al. |
| 2004/0069717 A1 | 4/2004 | Laurell et al. |
| 2004/0139792 A1 | 7/2004 | Cobb |
| 2005/0072677 A1 | 4/2005 | Gascoyne et al. |
| 2005/0097968 A1 * | 5/2005 | Ishikawa et al. ............... 73/861 |
| 2006/0006769 A1 * | 1/2006 | Masters et al. ............... 310/367 |
| 2006/0021437 A1 | 2/2006 | Kaduchak et al. |
| 2006/0034733 A1 | 2/2006 | Ferren et al. |
| 2006/0071580 A1 * | 4/2006 | Sawada ...................... 310/369 |
| 2006/0163166 A1 | 7/2006 | Hawkes et al. |
| 2007/0037172 A1 | 2/2007 | Chiu et al. |
| 2007/0071683 A1 | 3/2007 | Dayton et al. |
| 2007/0098232 A1 | 5/2007 | Matula et al. |
| 2007/0119239 A1 | 5/2007 | Priev et al. |
| 2007/0263693 A1 | 11/2007 | Essaian et al. |
| 2008/0053787 A1 | 3/2008 | Bagajewicz |
| 2008/0106736 A1 | 5/2008 | Graves et al. |
| 2008/0245709 A1 | 10/2008 | Kaduchak et al. |
| 2008/0245745 A1 | 10/2008 | Ward et al. |
| 2009/0029870 A1 | 1/2009 | Ward et al. |
| 2009/0038932 A1 * | 2/2009 | Denslow et al. ......... 204/157.15 |
| 2009/0042239 A1 | 2/2009 | Ward et al. |
| 2009/0042310 A1 | 2/2009 | Ward et al. |
| 2009/0045107 A1 | 2/2009 | Ward et al. |
| 2009/0048805 A1 | 2/2009 | Kaduchak et al. |
| 2009/0050573 A1 | 2/2009 | Ward et al. |
| 2009/0053686 A1 | 2/2009 | Ward et al. |
| 2009/0107241 A1 | 4/2009 | Goddard et al. |
| 2009/0139332 A1 | 6/2009 | Goddard et al. |
| 2009/0158823 A1 | 6/2009 | Kaduchak et al. |
| 2009/0162887 A1 | 6/2009 | Kaduchak et al. |
| 2009/0227042 A1 | 9/2009 | Gauer et al. |
| 2009/0316151 A1 | 12/2009 | Matula et al. |
| 2010/0000325 A1 | 1/2010 | Kaduchak et al. |
| 2010/0009333 A1 | 1/2010 | Auer |
| 2011/0024335 A1 | 2/2011 | Ward et al. |
| 2011/0032522 A1 | 2/2011 | Graves et al. |
| 2011/0134426 A1 | 6/2011 | Kaduchak et al. |

FOREIGN PATENT DOCUMENTS

| | | |
|---|---|---|
| DE | 3027433 | 2/1982 |
| EP | 0 147 032 | 3/1985 |
| EP | 0 773 055 A2 | 5/1997 |
| EP | 1416239 | 5/2004 |
| GB | 500271 | 12/1937 |
| JP | 63139231 A | 6/1988 |
| JP | 01-112161 | 4/1989 |
| JP | 06241977 A | 9/1994 |
| JP | 08266891 A | 10/1996 |
| JP | 11-014533 | 1/1999 |
| JP | 11014533 A * | 1/1999 |
| WO | WO 88/09210 | 12/1988 |
| WO | WO 90/05008 | 5/1990 |
| WO | WO 94/29695 | 12/1994 |
| WO | WO 97/02482 A | 1/1997 |
| WO | WO 00/41794 | 7/2000 |
| WO | WO-02059577 | 8/2002 |
| WO | WO 02/072234 A1 | 9/2002 |
| WO | WO 02/072236 A1 | 9/2002 |
| WO | WO 03/079006 A1 | 9/2003 |
| WO | WO 2004/024287 A1 | 3/2004 |

(56) References Cited

FOREIGN PATENT DOCUMENTS

| WO | WO 2004/033087 A1 | 4/2004 |
|---|---|---|
| WO | WO-2004/048948 | 6/2004 |
| WO | WO2006/032703 | 3/2006 |
| WO | WO-2006/076195 | 7/2006 |
| WO | WO 2007/128795 A2 | 11/2007 |
| WO | WO 2008/122051 A1 | 10/2008 |
| WO | WO 2009/091925 A2 | 7/2009 |
| WO | WO-2011/068764 | 6/2011 |

OTHER PUBLICATIONS

Bardsley et al., "Electroacoustic production of murine hybridomas," Journal of Immunological Methods, 129(1):41-47 (1990).
Haake et al., "Positioning, Displacement, and Localization of Cells Using Ultrasonic Forces," Biotechnology and Bioengineering, 92(1):8-14 (2005).
Hawkes et al., "Continuous cell washing and mixing driven by an ultrasound standing wave within a microfluidic channel," Lab Chip, 4:446-452 (2004).
Kumar et al., "Fractionation of Cell Mixture Using Acoustic and Laminar Flow Fields," Wiley Periodicals, Inc. (2004).
Petersson et al., "Carrier medium exchange through ultrasonic particle switching in microfluidic channels," Analytical Chemistry 77:1216-1221 (2005).
Yagi et al., "Flow Cytometry to Evaluate *Theileria sergenti* Parasitemia Using the Fluorescent Nucleic Acid Stain, SYTO16," Cytometry 41:223-225 (2000).
Extended European search report in Application No. 08733084.1, dated Mar. 24, 2010.
International search report in International application No. PCT/US08/87579, dated Feb. 9, 2009.
International search report in International application No. PCT/US2008/059181, dated Jul. 25, 2008.
International search report in International application No. PCT/US2009/031154, dated Jul. 8, 2009.
Aboobaker, N. et al., "Mathematical modeling of the movement of suspended particles subjected to acoustic and flow fields", *App. Math. Modeling* 29 2005, 515-532.
Anderson, M. et al., "The Physics and Technology of Ultrasonic Particle Separation in Air", *WCU* 2003, 1615-1621.
Apfel, R. E., "Acoustic Radiation Pressure—Principles and Application to Separation Science", *Fortschritte Der Akustik DAGA '90* 1990, 19-30.
Araz, Muhammet K. et al., "Ultrasonic Separation in Microfluidic Capillaries", *IEEE Ultrasonics Symposium* 2003, 1066-1069.
Asai, K. et al., "Ultrasonic treatment of slurry", *Third International Coal Preparation Conference* 1958, 518-527.
Barmatz, M. et al., "Acosutic radiation potential on a sphere in plane, cylindrical, and spherical standing wave fields", *J. Acoust. Soc. Am.* 77 1985, 928-945.
Bauerecker, Sigurd et al., "Formation and growth of ice particles in stationary ultrasonic fields", *J. of Chem. Phys.* 1998, 3709-3712.
Bazou, Despina et al., "Physical Environment of 2-D Animal Cell Aggregates Formed in a Short Pathlength Ultrasound Standing Wave Trap", *Ultrasound in Med. & Biol.* 31 2005, 423-430.
Benes, E., "Improved quartz crystal microbalance technique", *J. Appl. Phys.* 56 1984, 608-626.
Beverloo, H. B. et al., "Inorganic Phsophors as New Luminescent Labels for Immunocytochemistry and Time-Resolved Microscopy", *Cytometry* 11 1990, 784-792.
Bienvenue, Joan M. et al., "Microchip-Based Cell Lysis and DNA Extraction from Sperm Cells for Application to Forensic Analysis", *J. Forensic Sci.* 51 2006, 266-273.
Binks, Bernard P., "Modern Aspects of Emulsion Science", *The Royal Society of Chemistry* 1998, 310-321.
Bishop, J. E. et al., "Mechanism of higher brightness of PerCP-Cy5. 5", *Cytometry Supp* vol. 10 2000, 162-163.
Borthwick, K. A. et al., "Development of a novel compact sonicator for cell disruption", *J. of Microbiological Methods* 60 2005, 207-216.

Bosma, Rouke et al., "Ultrasound, a new separation technique to harvest microlalgae", *J. Appl. Phycology 15* 2003, 143-153.
Bossuyt, Xavier et al., "Comparative Analysis for Whole Blood Lysis Methods for Flow Cytometry", *Cytometry 30* 1997, 124-133.
Brodeur, Pierre H., "Acoustic Separation in a Laminar Flow", *Ultrasonics Symposium* 1994, 1359-1362.
Caperan, PH. et al., "Acoustic Agglomeration of a Glycol Fog Aerosol: Influence of Particle Concentration and Intensity of the Sound Field at Two Frequencies", *J. Aerosol Sci. 26* 1995, 595-612.
Chase, Eric S. et al., "Resolution of Dimly Fluorescent Particles: A Practical Measure of Fluorescence Sensitivity", *Cytometry 33* 1998, 267-279.
Coakley, W. T. et al., "Analytical scale ultrasonic standing wave manipulation of cells and microparticles", *Ultrasonics 38* 2000, 638-641.
Coakley, W. T. et al., "Cell-cell contact and membrane spreading in an ultrasound trap", *Colloids and Surfaces B: Biointerfaces 34* 2004, 221-230.
Coakley, W. T. et al., "Ultrasonic separations in analytical biotechnology", *Tibtech 15* 1997, 506-511.
Condrau, Marc A. et al., "Time-Resolved Flow Cytometry for the Measurement of Lanthanide Chelate Fluorescence: I. Concept and Theoretical Evaluation", *Cytometry 16* 1994, 187-194.
Condrau, Marc A., "Time-Resolved Flow Cytometry for the Measurement of Lanthanide Chelate Fluorescence: II. Instrument Design and Experimental Results", *Cytometry 16* 1994, 195-2005.
Cousins, C. M. et al., "Plasma Preparation from Whole Blood Using Ultrasound", *Ultrasound in Med. & Biol. 26* 2000, 881-888.
Curtis, H. W., "Ultrasonic Continuous Flow Plasmapheresis Separator", *IBM Tech. Disc. Bulletin 25* 1982, 192-193.
Czyz, Henryka, "On the Concentration of Aerosol Particles by Means of Drift Forces in a Standing Wave Field", *Acustica 70* 1990, 23-28.
Dain, Y. et al., "Dynamics of Suspended Particles in a Two-Dimensional High-Frequency Sonic Field", *J. Aerosol Sci. 26* 1995, 575-594.
Dain, Y., "Side drift of aerosols in two-dimensional resonant acoustic levitators", *J. Acoust. Soc. Am 102* 1997, 2549-2555.
Danilov, S. D. et al., "Mean force on a small sphere in a sound field in a viscous fluid", *J. Acoust. Soc. Am. 107* 2000, 143-153.
Danilov, S. D., "The Mean Force Acting on a Small Body in an Axisymmetric Sound Field in a Real Medium", *Izvestiya Adademii Nauk SSSR, Mekhanika Zhidkosti I Gaza 5* 1985, 812-820.
Dean, Phillip N. et al., "Hydrodynamic Orientation of Sperm Heads for Flow Cytometry", *Biophys. J. 23* 1978, 7-13.
Doblhoff-Dier, O. et al., "A Novel Ultrasonic Resonance Field Device for the Retention of Animal Cells", *Biotechnol. Prog. 10* 1994, 428-432.
Doinikov, Alexander A., "Acoustic radiation force on a spherical particle in a viscous heat-conducting fluid. I. General formula", *J. Acoust. Soc. Am. 101* 1997, 713-721.
Doinikov, Alexander A., "Acoustic radiation force on a spherical particle in a viscous heat-conducting fluid. II. Force on a rigid sphere", *J. Acoust. Soc. Am. 101* 1997, 722-730.
Doinikov, Alexander A., "Acoustic radiation force on a spherical particle in a viscous heat-conducting fluid. III. Force on a liquid drop", *J. Acoust. Soc. Am. 101* 1997, 731-740.
Doinikov, A. A., "Acoustic radiation pressure on a rigid sphere in a viscous fluid", *Proc. R. Soc. Lond. 447* 1994, 447-466.
Donnert, Gerald et al., "Major signal increase in fluorescence microscopy through dark-state relaxation", *Nature Methods 4* 2007, 81-86.
Doornbos, Richard M. et al., "Experimental and Model Investigations of Bleaching and Saturation of Fluorescence in Flow Cytometry", *Cytometry 29* 1997, 204-214.
Fenniri, Hicham et al., "Classification of Spectroscopically Encoded Resins by Raman Mapping and Infrared Hyperspectral Imaging", *Journal of Combinatorial Chemistry 8* 2006, 192-198.
Fulwyler, Mack J., "Hydronamic Orientation of Cells", *Histochem. Cytoche. 7* 1977, 781-783.
Gaida, TH. et al., "Selective Retention of Viable Cells in Ultrasonic Resonance Field Devices", *Biotech. Prog. 12* 1996, 73-76.
Gallego Juarez, J. A. et al., "Piezoelectric Transducer for Air-Borne Ultrasound", *Acustica 29* 1973, 234-239.

(56) References Cited

OTHER PUBLICATIONS

Gao, Xiaohu et al., "Quantum Dot-Encoded Mesoporous Beads with High Brightness and Uniformity: Rapid Readout Using Flow Cytometry", *Anal. Chem. 76* 2004, 2406-2410.

Gherardini, Lisa et al., "A New Immobilisation Method to Arrange Particles in a Gel Matrix by Ultrasound Standing Waves", *Ultrasound in Med. & Biol.* 31 2005, 261-272.

Goddard, Gregory et al., "Single Particle High Resolution Spectral Analysis Flow Cytometry", *Cytometry 69A* 2006, 842-851.

Goddard, Gregory R., "Ultrasonic Concentration in a Line Driven Cylindrical Tube", *Dissertation* 2004, 1-276.

Goddard, Gregory et al., "Ultrasonic particle concentration in a line-driven cylindrical tube", *J. Acoust. Soc. Am. 117* 2005, 3440-3447.

Goddard, Gregory et al., "Ultrasonic Particle-Concentration for Sheathless Focusing of Particles for Analysis in a Flow Cytometer", *Cytometry 69* 2006, 66-74.

Gonzalez, Itziar et al., "Precise Measurements of Particle Entertainment in a Standing-Wave Acoustic Field Between 20 and 3500 Hz", *J. Aerosol Sci. 31* 2000, 1461-1468.

Gor'Kov, L. P. et al., "On the forces acting on a small particle in an acoustical field in an ideal fluid", *Soviet Physics-Doklady 6* 1962, 773-775.

Gould, R. K. et al., "The effects of acoustic forces on small aprticles in suspension", *Proceedings of the 1973 Symposium on Finite Amplitude Wave Effects in Fluids* Bjorno, L., ed., Pergamon, Guildford 1974, 252-257.

Gould, Robert K. et al., "Upper sound pressure limits on particle concentration in fields of ultrasonic standing-wave at megahertz frequencies", *Ultrasonics 30* 1992, 239-244.

Grossner, Michael T. et al., "Single fiber model of particle retention in an acoustically driven porous mesh", *Ultrasonics 41* 2003, 65-74.

Grossner, Michael T. et al., "Single-Collector Experiments and Modeling of Acoustically Aided Mesh Filtration", *Amer. Inst. Of Chem. Eng. 51* 2005, 1590-1598.

Grossner, Michael T. et al., "Transport analysis and model for the performance of an ultrasonically enhanced filtration process", *Chem. Eng. Sci. 60* 2005, 3233-3238.

Gupta, Sanjay et al., "Acoustically driven collection of suspended particles within porous media", *Ultrasonics 35* 1997, 131-139.

Gupta, Sanjay et al., "Fractionation of Mixed Particulate Solids According to Compressibility Using Ultrasonic Standing Wave Fields", *Chem. Eng. Sci. 50* 1995, 3275-3284.

Haake, Albrecht et al., "Contactless micromanipulation of small particles by an ultrasound field excited by a vibrating body", *J. Acoust. Soc. Am. 117* 2005, 2752-2760.

Haake, Albrecht et al., "Manipulation of Cells Using an Ultrasonic Pressure Field", *Ultrasound in Med. & Biol. 31* 2005, 857-864.

Haake, A. et al., "Positioning of small particles by an ultrasound field excited by surface waves", *Ultrasonics 42* 2004, 75-80.

Habbersett, Robert C. et al., "An Analytical System Based on a Compact Flow Cytometer for DNA Fragment Sizing and Single Molecule Detection", *Cytometry 60A* 2004, 125-134.

Hager, F. et al., "A Summary of All Forces Acting on Spherical Particles in a Sound Field", *Proc. of the Ultrasonic International '91 Conference and Exhibition*, Le Touquet, France 1991, 1-4.

Hamilton, Mark F. et al., "Acoustic streaming generated by standing waves in two-dimensional channels of arbitrary width", *J. Acoust. Soc. Am. 113* 2003, 153-160.

Hamilton, Mark F. et al., "Linear and nonlinear frequency shifts in acoustical resonators with varying cross sections", *J. Acoust. Soc. Am. 110* 2001, 109-119.

Hancock, Andrew, "Observation of Forces on Microparticles in Acoustic Standing Waves", *Thesis, submitted in partial satisfaction of the quirements for the degree of Master of Science in Biomedical Engineering, University of California*, Davis 2001, 1-155.

Harma, Harri et al., "Zeptomole detection sensitivity of prostate-specific antigen in a rapid microtitre plate assay using time-resolved fluorescence", *Luminescence 15* 2000, 351-355.

Harris, N. R. et al., "A silicon microfluidic ultrasonic separator", *Sensors and Actuators 95* 2003, 425-434.

Harrison, Benjamin S. et al., "Near-Infrared Photo- and Electroluminescence of Alkoxy-Substituted Poly (p-phenylene) and Nonconjugated Polymer/Lanthanide Tetraphenylporphyrin Blends", *Chemistry of Materials 16* 2004, 2938-2947.

Hatanaka, Shin-Ichi et al., "Effect of Process Parameters on Ultrasonic Separation of Dispersed Particles in Liquid", *Jpn. J. Appl. Phys. 38* 1999, 3096-3100.

Hawkes, Jeremy J. et al., "A laminar flow expansion chamber facilitating downstream manipulation of particles concentrated using an ultrasonic standing wave", *Ultrasonics 36* 1998, 901-903.

Hawkes, Jeremy J. et al., "Force field particle filter, combinin ultrasound standing waves and laminar flow", *Sensors and Actuators B 75* 2001, 213-222.

Hawkes, Jeremy J. et al., "Microparticle manipulation in millimetre scale ultrasonic standind wave chambers", *Ultrasonics 36* 1998, 925-931.

Hawkes, Jeremy J. et al., "Single half-wavelength ultrasonic particle filter: Predictions of the transfer matrix multilayer resonator model and experimental filtration results", *J. Acoust. Soc. Am. 111* 2002, 1259-1266.

Hawkes, Jeremy J. et al., "Ultrasonic deposition of cells on a surface", *Biosensors and Bioelectronics 19* 2004, 1021-1028.

Hemmila, I. et al., "Progress in Lanthanides as Luminescent Probes", *J. Fluoresncence 15* 2005, 529-542.

Hertz, H. M., "Standing-wave acoustic trap for nonintrusive positioning of microparticles", *J. Appl. Phys. 78* 1995, 4845-4849.

Higashitani, KO et al., "Migration of Suspended Particles in Plane Stationary Ultrasonic Field", *Chem. Eng. Sci. 36* 1981, 1187-1192.

Hill, Martyn et al., "Modelling in the design of a flow-through ultrasonic separator", *Ultrasonics 38* 2000, 662-665.

Hill, Martyn et al., "Modelling of layered resonators for ultrasonic separation", *Ultrasonics 40* 2002, 385-392.

Hill, Daniel H. et al., "Operating Characteristics of Acoustically Driven Filtration Processes for Particulate Suspensions", *Sep. Sci. and Tech. 35* 2000, 1363-1375.

Hill, Martyn, "The selection of layer thicknesses to control acoustic radiation forces profiles in layered resonators", *J. Acoust. Soc. Am. 114* (5) 2003, 2654-2661.

Hirschfeld, Tomas, "Fluorescence Background Discrimination by Prebleaching", *J. Histochem. and Cytochem. 27* 1979, 96-101.

Holmes, David et al., "High throughput particle analysis: Combining dielectrophoretic particle focussing with confocal optical detection", *Biosensors and Bioelectronics 21* 2006, 1621-1630.

Holwill, Ian L., "The use of ultrasonic standing waves to enhance optical particle sizing equipment", *Ultrasonics 38* 2000, 650-653.

Huhtinen, Petri et al., "Synthesis, Characterization, and Application of Eu(III), Tb(III), Sm (III), and Dy(III) Lanthanide Chelate Nanoparticle Labels", *Anal. Chem. 77* 2005, 2643-2648.

Johnston, Paul A. et al., "Cellular platforms for HTS: three case studies", *DDT 7* 2002, 353-363.

Jonsson, Henrik et al., "Particle separation using ultrasound can be used with human shed mediastinal blodd", *Perfusion 20* 2005, 39-43.

Kaduchak, Gregory et al., "E6 diffraction catastrophe of the primary rainbow of oblate water drops: observations with white-light and laser illumination", *Applied Optics 33* 1994, 4691-4696.

Kaduchak, Gregory et al., "Hyperbolic umbilic and E6 diffraction catastrophes associated with the secondary rainbow of oblate water drops: observations with laser illumination", *Applied Optics 33* 1994, 4697-4701.

Kapishnikov, Sergey et al., "Continuous particle size separation and size sorting using ultrasound in a microchannel", *J. Stat. Mech.* 2006, 1-13.

Karumanchi, R. S. et al., "Field-assisted extraction of cells, particles and macromolecules", *Trends in Biotechnology* vol. 20, No. 2 Feb. 2002, 72-78.

Kaye, Paul H., "Spatial light-scattering analysis as a means of characterizing and classifying non-spherical particles", *Meas. Sci. Technol. 9* 1998, 141-149.

Kilburn, D. G. et al., "Enhanced Sedimentation of Mammalian Cells following Acoustic Aggregation", *Biotech. and Bioeng. 34* 1989, 559-562.

King, L. V., "On the acoustic radiation on spheres", *Proc. R. Soc. A.* vol. 147 1933, 212-240.

(56) References Cited

OTHER PUBLICATIONS

Kogan, Shulim et al., "Acoustic concentration of particles in piezoelectric tubes: Theoretical modeling of the effect of cavity shape and symmetry breaking", *J. Acoust. Soc. Am. 116* 2004 , 1967-1974.

Kozuka, Teruyuki et al., "Acoustic Micromanipulation Using a Multi-Electrode Transducer", *7th Inter. Symp. on Micro Machine and Human Science* IEEE 1996 , 163-170.

Kozuka, Teruyuki et al., "Control of a Standing Wave Field Using a Line-Focused Transducer for Two-Dimensional Manipulation of Particles", *Jpn. J. Appl. Phys. 37* 1998 , 2974-2978.

Kozuka, Teruyuki et al., "Micromanipulation Using a Focused Ultrasonic Standing Wave Field", *Electronics and Communications in Japan 83* 2000 , 1654-1659.

Kumar, Manoj et al., "Fractionation of Cell Mixtures Using Acoustic and Laminar Flow Fields", *Biotech. Bioeng. 89* 2005 , 129-137.

Kuznetsova, Larisa A. et al., "Cavitation buble-driven cell and particle behavior in a ultrasound standing wave", *J. Acoust. Soc. Am. 117* 2005 , 104-112.

Kuznetsova, Larisa A. et al., "Microparticle concentration in short path length ultrasonic resonators: Roles of radiation pressure and acoustic streaming", *J. Acoust. Soc. Am. 116* 2004 , 1956-1966.

Kwiatkowski, Christopher S. et al., "Resonator frequency shift due to ultrasonically induced microparticle migration in an aqueous suspension: Observations and model for the maximum frequency shift", *J. Acoust. Soc. Am. 103* 1998 , 3290-3300.

Leif, Robert C. et al., "Increasing the Luminescence of Lanthanide Complexes", *Cytometry 69A* 2006 , 767-778.

Leif, R. C. et al., "Markers for Instrumental Evaluation of Cells of the Female Reproductive Tract; Existing and New Markers", in *The Automation of Uterine Cancer Cytology* (edited by G. L. Wied, G. F. Babr, P.H. Bartels). *Tutorials of Cytology* 1976 , 313-344.

Lierke, E. G. et al., "Acoustic Positioning for Space Processing of Materials Science Samples in Mirror Furnaces", *IEEE Ultrasonics Symposium* 1983 , 1129-1139.

Lilliehorn, Tobias et al., "Trapping of microparticles in the rear field of an ultrasonic transducer", *Ultrasonics 43* 2005 , 293-303.

Lofstedt, Ritva et al., "Theory of long wavelength acoustic radiation pressure", *J. Acoust. Soc. Am. 90* 1991 , 2027-2033.

Loken, Michael R. et al., "Cell Discrimination by Multiangle Light Scattering", *Histochem. Cytochem. 24* 1976 , 284-291.

Loken, Michael R. et al., "Identification of Cell Asymmetry and Orientation by Light Scattering", *Histochem. Cytochem. 7* 1977 , 790-795.

Macey, M. G. et al., "Comparative Study of Five Commercial Reagents for Preparing Normal and Leikaemic Lymphoctyes for Immunophenotypic Analysis by Flow Cytometry", *Cytometry 38* 1999 , 153-160.

Maltsev, Valeri P. , "Scanning flow cytometry for individual particle analysis", *Review of Scientific Instruments 71* 2000 , 243-255.

Mandralis, Z. , "Enhanced synchronized ultrasonic and flow-field fractionation of suspensions", *Ultrasonics 32* 1994 , 113-121.

Mandralis, Z. I. et al., "Transient Response of Fine Particle Suspensions to Mild Planar Ultrasonic Fields", *Fluid/Particle Separation Journal* 1990 , 115-121.

Marston, Philip L. et al., "Generalized rainbows and unfolded glories of oblate drops: organization for multiple internal reflection and extension of cusps into Alexander's dark band", *Applied Optics 33* 1994 , 4702-4713.

Marston, Philip L. et al., "Manipulation of Fluid Objects with Acoustic Radiation Pressure", *Ann. N.Y. Acad. Sci. 1027* 2004 , 414-434.

Marston, P. L. et al., "Resonances, Radiation Pressure, and Optical Scattering Phenomena of Drops and Bubbles", *Proceedings of the Second Internaitonal Colloquium on Drops and Bubbles, Jet Prop. Lab. Pub 82-7* Pasadena, CA. 1982 , 166-174.

Martin, K. M. et al., "Acoustic filtration and sedimentation of soot particles", *Experiments in Fluids 23* 1997 , 483-488.

Masudo, Takashi et al., "Particle Characterization and Separation by a Coupled Acoustic-Gravity Field", *Analytical Chemistry 73* 2001 , 3467-3471.

Mathies, Richard A. et al., "Optimization of High-Sensitivity Fluorescence Detection", *Anal. Chem. 62* 1990 , 1786-1791.

Mazumdar, M. K. et al., "Spart Analyzer: Its Application to Aerodynamic Size Distribution Measurement", *J. Aerosol Sci. 10* 1979 , 561-569.

Mazumder, M. K. et al., "Single particle aerodynamic relaxation time analyzer", *Rev. Sci. Instrum. 48* 1977 , 622-624.

Meindersma, G. W. et al., "Separation of a biocatalyst with ultrafiltration or filtration after bioconversion", *J. Membrane Sci. 125* 1997 , 333-349.

Morgan, J. et al., "Manipulation of in vitro toxicant sensors in an ultrasonic standing wave", *Toxicology in Vitro 18* 2004 , 115-120.

Mullaney, P.F. et al., "The Small Angle Light Scattering of Biological Cells", *Biophys. J. 10* 1970 , 764-772.

Neild, A. et al., "Design, modeling and characterization of microfluidic devices for ultrasonic manipulation", *Sensors and Actuators B: Chemical* vol. 121, Issue 2 Feb. 20, 2007.

Neukammer, Jorg et al., "Angular distribution of light scattered by single biological cells and oriented particle agglomerates", *Appl. Opt. 42* 2003 , 6388-6397.

Nilsson, Andreas et al., "Acoustic control of suspended particles in micro fluidic chips", *Lab Chip 4* 2004 , 131-135.

Nolan, John P. et al., "Suspension Array Technology: New Tools for Gene and Protein Analysis", *Cellular and Molecular Biology 47* 2001 , 1241-1256.

Nowotny, Helmut et al., "Layered piezoelectric resonators with an arbitrary number electrodes (general one-dimensional treatment)", *J. Acoust. Soc. Am. 90* 1991 , 1238-1245.

Otaki, Masahiro et al., "Virus Removal in a Membrane Separation Process", *Water Sci. and Tech. 37* 1998 , 107-116.

Pangu, Gautam D. et al., "Acoustically aided separation of oil droplets from aqueous emulsions", *Chem. Eng. Sci. 59* 2004 , 3183-3193.

Petersson, Filip et al., "Carrier Medium Exchange through Ultrasonic Particle Switching in Microfluidic Channels", *Anal. Chem. 77* 2005 , 1216-1221.

Petersson, Filip et al., "Continuous separation of lipid particles from erythrocytes by means of laminar flow and acoustic standing wave forces", Lab Chip 5 2005 , 20-22.

Petersson, Filip et al., "Free Flow Acoustophoresis: Microfluidic-Based Mode of Particle and Cell Separation", *Anal. Chem. 79* 2007 , 5117-5123.

Pregibon, Daniel C. et al., "Multifunctional Encoded Particles for High-Throughput Biomolecule Analysis", *Science 315* 2007 , 1393-1396.

Princen, Katrien et al., "Evaluation of SDF-1/CXCR4-Induced Ca2+ Signaling by Fluorometric Imaging Plate Reader (FLIPR) and Flow Cytometry", *Cytometry 51A* 2003 , 35-45.

Pui, Phylis W. et al., "Batch and Semicontinuous Aggregattion and Sedimentation of Hybridoma Cells by Acoustic Resonance Fields", *Biotechnol. Prog. 11* 1995 , 146-152.

Rao, G. V. Rama et al., "Monodisperse Mesoporous Silica Microspheres Formed by Evaporation-Induced Self Assembly of Surfacant Templates in Aerosols", *Advanced Materials 18* 2002 , 1301-1304.

Rens, Wim et al., "A Novel Nozzel for More Efficient Sperm Orientation to Improve Sorting Efficiency of X and Y Chromosome-Bearing Sperm", *Cytometry 33* 1998 , 476-481.

Ricks, D. C. et al., "A numerically stable global matrix method for cylindrically layered shells excited by ring forces", *J. Acoust. Soc. Am.* vol. 95 1994 , 3339-3349.

Rouleau, Francois , "Electromagnetic scattering by compact clusters of spheres", *Astron. Astrophys. 310* 1996 , 686-698.

Rudnick, Joseph et al., "Oscillational instabilities in single-mode acoustic levitators", *J. Acoust. Soc. Am. 87* 1990 , 81-92.

Saito, Mitsunori et al., "Microorganism manipulation and microparticle arrangement by the use of ultrasonic standing waves", *SPIE 4590* 2001 , 26-37.

Saito, Mitsunori et al., "Ultrasonic manipulation of locomotive microorganisms and evaluation of their activity", *J. App. Physics 92* 2002 , 7581-7586.

Saito, Mitsunori et al., "Ultrasonic trapping of paramecia and estimation of their locomotive force", *Appl. Phys. Lett 71* 1997 , 1909-1911.

(56) References Cited

OTHER PUBLICATIONS

Saito, Mitsunori et al., "Ultrasonic waves for fabricating lattice structure in composite materials", *SPIE 3786* 1999, 179-190.

Samiotaki, Martina et al., "Seven-Color Time-Resolved Fluorescence Hybridization Analysis of Human Papilloma Virus Types", *Analytical Biochemistry 253* 1997, 156-161.

Sato, Masanori et al., "Quantum mechanical representation of acoustic streaming and acoustic radiation pressure", *Physical Review E 64* 2001, 026311-1-026311-5.

Schmid, M. et al., "A computer-controlled system for the measurement of complete admittance spectra of piezoelectric resonators", *Meas. Sci. Technol. 1* 1990, 970-975.

Schoell, Wolfgang M. et al., "Separation of Sperm and Vaginal Cells with Flow Cytometry for DNA Typing After Sexual Assault", *Obstetrics and Gynecology 94* 1999, 623-627.

Semianov, K. A. et al., "Measurement of Mammalian Erythrocyte Indices from Light Scattering with Scaning Flow Cytometer", *Proc. SPIE 5141* 2003, 106-113.

Sethu, Palaniappan et al., "Continuous Flow Microfluidic Device for Rapid Erythrocyte Lysis", *Anal. Chem. 76* 2004, 6247-6253.

Shapiro, Howard M., "Practical Flow Cytometry", Hoboken, NJ, *John Wiley & Sons, Inc.* 2005, 9-13.

Shvalov, Alexander N. et al., "Individual *Escherichia coli* Cells Studied from Light Scattering with the Scanning Flow Cytometer", *Cytometry 41* 2000, 41-45.

Shvalov, Alexander N. et al., "Light -scattering properties of individual erythrocytes", *Applied Optics 38* 1999, 230-235.

Simpson, Harry J. et al., "Ultrasonic four-wave mixing mediated by an aqueous suspension of microspheres: Theoretical steady-state properties", *J. Acoust. Soc. Am. 98* 1995, 1731-1741.

Slomkowski, Stanislaw et al., "New Typed of Microspheres and Microsphere-related Materials for Medical Diagnostics", *Polymers for Advanced Technologies 13* 2002, 906-918.

Sobanski, Michael A. et al., "Sub-micron particle manipulation in an ultrasonic standing wave: Applications in detection of clinically important biomolecules", *Bioseparation 9* 2001, 351-357.

Steinkamp, J. A. et al., "Enhanced Immunofluorescence Measurement Resolution of Surface Antigens on Highly Autofluorescent, Glutaraldehyde-Fixed Cells Analyzed by Phase-Sensitive Flow Cytometry", *Cytometry 37* 1999, 275-283.

Stoffel, C. L. et al., "Data Analysis for a Dual Analysis for a Dual-Channel Virus Counter", *Analytical Chemistry* vol. 7, Dept. of Chemistry & Biochemistry, University of Colorado 2005.

Stoffel, C. L. et al., "Design and Characterization of a Compact Dual Channel Virus Counter", *Cytometry Part A 65A* Dept. of Chemistry and Biochemistry, University of Colorado, 140-147.

Stovel, Richard T. et al., "A Means for Orienting Flat Cells in Flow Systems", *Biophys. J. 23* 1978, 1-5.

Takeuchi, Masao et al., "Ultrasonic Micromanipulation of Small Particles in Liquid", *Jpn. J. Appl. Phys. 33* 1994, 3045-3047.

Takeuchi, Masao et al., "Ultrasonic Micromanipulator Using Visual Feedback", *Jpn. J. Appl. Phys. 35* 1996, 3244-3247.

Thiessen, David B. et al., "Principles of some Acoustical, Electrical, and Optical Manipulation Methods with Applications to Drops, Bubbles, and Capillary Bridges", *ASME Fluids Eng. Div. Publ. FED* 1998.

Thiessen, David B. et al., "Some Responses of Small Diffusion Flames to Ultrasonic Radiation", *NASA* 2003, 321-324.

Tolt, Thomas L. et al., "Separation devices based on forced coincidence response of fluid-filled pipes", *J. Acoust. Soc. Am. 91* 1992, 3152-3156.

Tolt, Thomas L. et al., "Separation of Dispersed Phases from Liquids in Acoustically Driven Chambers", *Chem. Eng. Science 48* 1993, 527-540.

Townsend, R. J. et al., "Modelling of particle paths passing through an ultrasonic standing wave", *Ultrasonics 42* 2004, 319-324.

Trihn, E. H. et al., "Experimental study of streaming flows associated with ultrasonic levitators", *Phys. Fluids 6* 1994, 3567-3579.

Trinh, E. H., "Compact acoustic levitation device for studies in fluid dynamics and material science in the laboratory and microgravity", *Rev. Sci. Instrum. 56* 1985, 2059-2065.

Tuckermann, Rudolf et al., "Trapping of heavy gases in stationary ultrasonic fields", *Chem. Phys. Ltrs. 363* 2002, 349-354.

Tung, Yi-Chung et al., "PDMS-based opto-fluidic micro flow cytometer with two-color, multi-angle fluorescence detection capability using PIN photodiodes", *Sensors and Actuators 98* 2004, 356-367.

Vainshtein, P. et al., "On the Drift of Aerosol Particles in Sonic Fields", *J. Aerosol Sci. 23* 1992, 631-637.

Vainshtein, P. et al., "The effect of centreline particle concentration in a wave tube", *J. Fluid Mech. 306* 1996, 31-42.

Van Hee, P. et al., "Strategy for Selection of Methods for Separation of Bioparticles From Particle Mixtures", *Biotech. Bioeng. 94* 2006, 689-709.

Verpoorte, Elisabeth, "Beads and chips: new recipes for analysis—Elisabeth Verpoorte reviews particle handling in microchannels", *Lab Chip 3* 2003, 60N-68N.

Visuri, S. V. et al., "Microfluidic tolls for biological sample preparation", *Poster 1423, 2nd Annual International IEEE-EMBS Special Topic Cofnerence on Microtechnologies in Medicine & Biology*, May 2-24, 2002, 556-559.

Wang, Zhaowei et al., "Retention and Viability Characteristics of Mammalian Cells in an Acoustically Driven Polymer Mesh", *Biotechnol. Prog. 20* 2004, 384-387.

Ward, Michael, "Manipulation of Immunomagnetic Targets in Microfluidic Channel Flow", *Dissertation* 2005, 1-205.

Weiser, Mary Ann H. et al., "Extension of acoustic levitation to include the study of micron-size particles in a more compressible host liquid", *J. Acoust. Soc. Am. 71* 1982, 1261-1268.

Weiser, M. A. et al., "Interparticle Forces on Red Cells in a Standing Wave Field", *Acustica 56* 1984, 114-119.

Whitworth, Glenn et al., "Particle column formation in a stationary ultrasonic field", *J. Acoust. Soc. Am. 91* 1992, 79-85.

Whitworth, G. et al., "Transport and harvesting of suspended particles using modulated ultrasound", *Ultrasonics 29* 1991, 439-444.

Wu, Yang et al., "Diazo Coupling Method for Covalent Attachment of Proteins to Solid Substrates", *Bioconjugate Chem. 17* 2006, 359-365.

Yamakoshi, Yoshiki et al., "Micro particle trapping by opposite phases ultrasonic travelling waves", *Ultrasonics 36* 1998, 873-878.

Yasuda, Kenji, "Blood Concentration by Superposition of Higher Harmonics of Ultrasound", *Jpn. J. Appl. Phys. 36* 1997, 3130-3135.

Yasuda, Kenji et al., "Concentration and Fractionation of Small Particles in Liquid by Ultrasound", *Jpn. J. Appl. Phys. 34* 1995, 2715-2720.

Yasuda, Kenji et al., "Deoxyribonucleic acid concentration using acoustic radiation force", *J. Acoust. Soc. Am. 99* 1996, 1248-1251.

Yasuda, Kenji, "Non-destructive, non-contact handling method for biomaterials in micro-chamber by ultrasound", *Sensors and Actuators 64* 2000, 128-135.

Yasuda, Kenji et al., "Particle separation using acoustic radiation force and elecrostatic force", *J. Acoust. Soc. Am. 99* 1996, 1965-1970.

Yasuda, Kenji et al., "Using acousitc radiation force as a concentration method for erythrocytes", *J. Acoust. Soc. Am 102* 1997, 642-645.

Ye, Chao-Hong et al., "Preparation of three terbium complexes with p-aminobenzoic acid and investigation of crystal structure influence on luminescence property", *Journal of Solid State Chemistry 177* 2004, 3735-3742.

Yurkin, Maxim A. et al., "Experimental and theoretical study of light scattering by individual mature red blook cells by use of scanning flow cytometry and a discrete dipole approximation", *Applied Optics 44* 2005, 5249-5256.

Borisov, Sergey M. et al., "Blue LED Excitable Temperature Sensors Based on a New Eurpium (III) Chelate", *J. Fluoresc 18* 2008, 581-589.

Invitrogen, , "Fluo-4 NW Calcium Assay Kits (F36205, F36206)", *Product Information* 2006.

Invitrogen, , "Fluorophore selection guide for flow cytometry", *Cellular Analysis* 2007.

(56) References Cited

OTHER PUBLICATIONS

Lakowicz, Joseph R. et al., "On the Possibility of Long-Wavelength Long-Lifetime High-Quantum-Yield Luminophores", *Analytical Biochemistry 288* 2001, 62-75.
McCartin, Brian J., "A Numerical Procedure for 2D Acoustic Waveguides with Heated Walls", http://flux.aps.org/meetings/YR99/OSS99/abs/S700004.html 1999.
Petersson, Filip, "Particle Flow Switch Utilizing Ultrasonic Particle Switching in Microfluidic Channels", *7th International Conf on Miniaturizing Chem and Biochem Analysis Systems* 2003, 879-882.
Steinkamp, John A., "A Differential Amplifier Circuit for Reducing Noise in Axial Light Loss Measurements", *Cytometry 4* 1983, 83-87.
Steinkamp, John A. et al., "Dual-Laser, Differential Fluorescence Correction Method for Reducing Cellular Background Autofluorescence", *Cytometry 7* 1986, 566-574.
Stewart, Carleton C. et al., "Resolving Leukocytes Using Axial Light Loss", *Cytometry 10* 1989, 426-432.
Tyson, Daniel S. et al., "Ruthenium (II) complex with a notably long excited state lifetime", *The Royal Society of Chemistry* 2000, 2355-2356.
Yuan, Jingli et al., "Lanthanide-based luminescence probes and time-resolved luminescence bioassays", *Trends in Analytical Chemistry 25* 2006, 490-500.
Borgnis, F.E., "Acoustic Radiation Pressure of Plane Compressional Waves", Review of Modern Physics (1953) 25:653-064.
Eurasian Patent Office Search Report in Eurasian Application No. 201001165, dated Jun. 2, 2011 (1 page).
Office Action in U.S. Appl. No. 12/239,501 mailed Nov. 1, 2010.
Biosep: The Advanced Acoustic Cell Retention Device, (Oct. 2002).
Benes, E., et al., "Separation of Dispersed Particles by Ultrasonic-Induced Coagulation," 15th Conference of the German Society for Acoustics, 1989, p. 1-2.
Groschi, M., et al., "Automatic Frequency Control for Piezoelectric Resonators and their Implementation in the Acoustic Driftwave Resonator," Thesis implemented at the Institute for General Physics at the Technical University of Vienna, abstract, 1991, p. 1-2.

Response to Mar. 24, 2010 Extended European Search Report for European Application No. 08733084.1 filed Jun. 16, 2010.
Office Action in U.S. Appl. No. 12/239,453 mailed Apr. 5, 2010.
Office Action in U.S. Appl. No. 12/239,453 mailed Aug. 12, 2010.
Office Action in U.S. Appl. No. 12/239,467 mailed May 10, 2011.
Office Action in U.S. Appl. No. 12/239,483 mailed Aug. 25, 2009.
Office Action in U.S. Appl. No. 12/239,483 mailed Nov. 8, 2010.
Office Action in U.S. Appl. No. 12/239,501 mailed May 24, 2011.
Office Action in U.S. Appl. No. 12/239,513 mailed Mar. 5, 2010.
Office Action in U.S. Appl. No. 12/239,513 mailed Oct. 28, 2009.
Office Action in U.S. Appl. No. 12/239,513 mailed Jan. 21, 2011.
Office Action in U.S. Appl. No. 12/239,453 mailed Jan. 27, 2010.
Office Action in U.S. Appl. No. 12/239,483 mailed Apr. 28, 2010.
Office Action in U.S. Appl. No. 12/239,513 mailed Sep. 1, 2010.
Office Action in U.S. Appl. No. 12/239,390 mailed Dec. 16, 2009.
Office Action in U.S. Appl. No. 12/239,390 mailed Jan. 29, 2010.
Office Action in U.S. Appl. No. 12/239,390 mailed Aug. 5, 2010.
International written opinion in international application No. PCT/US08/87579, dated Jul. 26, 2010.
Kundt et al., "Ueber longitudinale Schwingungen und Klangfiguren in cylindrischen Flüssigkeitssäulen," Annalen der Physik und Chemie, 153(9):1-13 (1874), with full English translation.
Petersson et al., "Separation of lipids from blood utilizing ultrasonic standing waves in microfluidic channels," Analyst, 129:938-943 (2004).
Skudrzyk et al., "Die Grundlagen der Akustic," Springer Verlag, pp. 202-205 and 807-825 (1954), with full English translation.
Cheung et al., "Impedance Spectroscopy Flow Cytometry: On-Chip Label-Free Cell Differentiation," Cytometry Part A, 65A:124-132 (2005).
Keij et al., "Coincidence in High-Speed Flow Cytometry: Models and Measurements," Cytometry, 12:398-404 (1991).
Marston, "Tensile Strength and Visible Ultrasonic Cavitation of Superfluidic $^4$He," Journal of Low Temperature Physics, 25 (3/4): 383-407 (1976).
Nield, et al. "A Micro-Particle Positioning Technique Combining an Ultrasonic Manipulator and a Microgripper," Journal of Micromechanical Microengineering, 16:1562-1570 (2006).

* cited by examiner

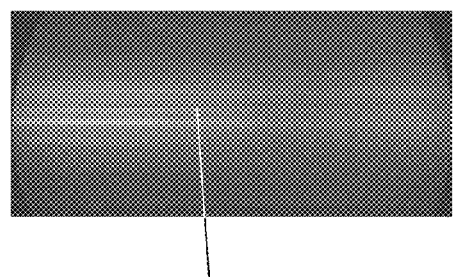 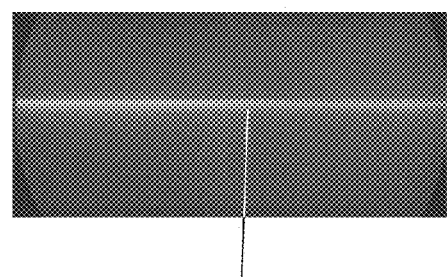
Figure 6A
Figure 6B

SYSTEM AND METHOD FOR ACOUSTIC FOCUSING HARDWARE AND IMPLEMENTATIONS

CROSS-REFERENCE TO RELATED APPLICATIONS

This application claims priority to and the benefit of U.S. Provisional Patent Application Ser. No. 61/021,443, entitled "System and Method for Acoustic Focusing Hardware and Implementations", to Kaduchak, filed on Jan. 16, 2008, and the specification thereof is incorporated herein by reference.

BACKGROUND OF THE INVENTION

1. Field of the Invention (Technical Field)

Embodiments of the present invention relate to acoustic cytometry and more specifically to acoustic focusing hardware and implementations.

2. Background

Note that the following discussion refers to a number of flow cytometry systems. Discussion of such systems herein is given for more complete background and is not to be construed as an admission that such systems are prior art for patentability determination purposes.

Flow cytometry is a powerful tool used for analysis of particles and cells in a myriad of applications primarily in bioscience research and medicine. The analytical strength of the technique lies in its ability to parade single particles (including bioparticles such as cells, bacteria and viruses) through the focused spot of light sources, typically a laser or lasers, in rapid succession, at rates exceeding thousands of particles per second. The high photon flux at this focal spot produces scatter of light by a particle and/or emission of light from the particle or labels attached to the particle that can be collected and analyzed. This gives the user a wealth of information about individual particles that can be quickly parleyed into statistical information about populations of particles or cells.

In traditional flow cytometry, particles are flowed through the focused interrogation point where a laser directs a laser beam to a focused point that includes the core diameter within the channel. The sample fluid containing particles is hydrodynamically focused to a very small core diameter of around 10-50 microns by flowing sheath fluid around the sample stream at a very high volumetric rate on the order of 100-1000 times the volumetric rate of the sample. This results in very fast linear velocities for the focused particles on the order of meters per second. This in turn means that each particle spends a very limited time in the excitation spot, often only 1-10 microseconds. When the linear flow of the hydrodynamic sheath fluid is stopped, the particles are no longer focused. Only resuming the hydrodynamic sheath fluid flow will refocus the particles. Further, once the particle passes the interrogation point the particle cannot be redirected to the interrogation point again because the linear flow velocity cannot be reversed. Still further, a particle cannot be held at the interrogation point for a user defined period of time for further interrogation because focusing is lost without the flow of the hydrodynamic sheath fluid. Because of the very high photon flux at the excitation point, flow cytometry is still a very sensitive technique, but this fast transit time limits the sensitivity and resolution that can be achieved. Often, greater laser power is used to increase the photon flux in an effort to extract more signal but this approach is limiting in that too much light can often photobleach (or excite to non-radiative states) the fluorophores being used to generate the signal and can increase background Rayleigh scatter, Raman scatter and fluorescence as well.

Slower flowing cytometry systems have been developed to push the limits of sensitivity and have shown detection limits down to the single molecule level. In one of these systems, it was shown that lower laser power (<1 mW) was actually preferable for single molecule detection of double stranded DNA fragments intercalated with fluorescent dyes. Because of the slow transit times (hundreds of microseconds to milliseconds), it was possible to get maximum fluorescence yield out of the dyes while reducing background, photobleaching and non-radiative triplet states with the lower laser power.

Slow flow hydrodynamic systems, while incredibly sensitive, are not in widespread use because fluidic dimensions are generally very small, which results in easy clogging and very limited sample throughput. In order to focus the sample stream to a core diameter small enough to maintain the uniform illumination and flow velocity required for precision particle measurement, the sheath must still be supplied in a very high volumetric ratio to the sample. In order to achieve a slow linear velocity, the volumetric sample rate must be extremely small. Therefore, to process appreciable numbers of events, the sample must be highly concentrated. If for example a relatively slow linear velocity of 1 centimeter per second is desired with a typical core diameter of about 10 microns, the sample must be delivered at about 0.05 microliters per minute. To process just 100 cells per second, the cell concentration must be 120,000 per microliter or 120 million per milliliter. This concentration requirement in turn makes clogging even more likely. The problem is further compounded by the tendency of many types of cells to clump in high concentration and to settle out and stick to surfaces when sample delivery rates are slow. The system created by Doornbos, circumvents the clogging problem by using a conventional flow cell with flow resistors to slow the flow, but he found it very difficult to control precise focused delivery of the sample. This method also does not eliminate the need for slow volumetric delivery and highly concentrated samples.

Sheathless, non-focusing flow cytometers have been developed but these instruments suffer from low sensitivity due to the need for a focal spot size that will excite particles throughout the channel. The spot size is reduced by using very small capillary channels but particles flow within the channel at variable rates according to the laminar flow profile that develops in the channel. This results in different transit times and coincidence of particles in the laser spot which both make analysis more difficult. Also, background cannot be reduced by spatially filtering optics that are designed to collect light from a tightly focused core stream. This limits sensitivity and resolution.

Other approaches have been demonstrated to manipulate particles using acoustic radiation pressure in a laboratory setting. These devices are planar devices modeled in Cartesian coordinates. Applying an acoustic field generates a quasi-one-dimensional force field that focuses particles into a ribbon in a rectangular chamber. For laminar flow, the resulting distribution of particles across the chamber places the particles in different velocity stream lines. Particles in different stream lines will not only be in different locations but they will also flow at different velocities. This in turn results in different residence times for particles at a location within the device. Planar focusing does not align particles in a manner suitable for use with flow cytometers.

BRIEF SUMMARY OF THE INVENTION

An embodiment of the present invention comprises an acoustic focusing capillary further comprising a capillary coupled to at least one vibration source and the at least one vibration source possessing a groove. The capillary of this embodiment is preferably coupled to the vibration source at the groove. The groove preferably has an approximately same cross-sectional geometry as the capillary. The capillary can be circular, elliptical, oblate, or rectangular. The vibration source preferably comprises a piezoelectric material. In this embodiment, the groove preferably increases an acoustic source aperture of the capillary.

Another embodiment of the present invention comprises a method of manufacturing an acoustic focusing capillary. This embodiment further comprises providing a capillary and at least one vibration source, machining a groove into the vibration source, and coupling the at least one vibration source to the capillary at the groove. The groove preferably has an approximately same cross-sectional geometry as the capillary. The capillary can be circular, elliptical, oblate, or rectangular. The at least one vibration source preferably comprises a piezoelectric material. This embodiment can optionally comprise increasing the acoustic source aperture of the capillary.

In yet another embodiment of the present invention, an apparatus that hydrodynamically and acoustically focuses particles in a particle stream comprises a flow chamber, an outer confine of the flow chamber for flowing a hydrodynamic fluid therethrough, a central core of the flow chamber for flowing the particle sample stream therethrough, and at least one transducer coupled to the chamber producing acoustic radiation pressure. The transducer of this embodiment is preferably coupled to an outer wall of the flow chamber. The transducer can alternatively form a wall of the flow chamber.

A further embodiment of the present invention comprises a method of hydrodynamically and acoustically focusing a particle stream. This method preferably comprises flowing a sheath fluid into outer confines of a capillary, flowing a particle stream into a central core of the capillary, and applying acoustic radiation pressure to the particle stream within the sheath fluid. The particle stream of this method can be hydrodynamically focused and subsequently acoustically focused. Alternatively, the particle stream is acoustically focused and hydrodynamically focused simultaneously.

Another method of hydrodynamically and acoustically focusing particles is still a further embodiment of the present invention. This embodiment preferably comprises providing a fluid comprising particles therein, flowing a sheath fluid into outer confines of a flow chamber, flowing the fluid containing the particles into a central core of the flow chamber, and applying acoustic radiation pressure to the fluid comprising the particles. This embodiment can also comprise analyzing the particles.

One embodiment of the present invention comprises a method of aligning particles using acoustic radiation pressure. This embodiment preferably includes providing a fluid comprising particles therein, subjecting the fluid to acoustic radiation pressure, rotating the fluid 90 degrees, and subjecting the fluid to acoustic radiation pressure a second time to align the particles. This embodiment can also comprise analyzing the aligned particles.

Another embodiment of the present invention comprises a method of hydrodynamically and acoustically focusing particles in a fluid. This embodiment includes flowing a fluid comprising particles therein, subjecting the fluid to acoustic radiation pressure in one planar direction to acoustically focus the particles, and flowing a sheath fluid in a second planar direction thereby hydrodynamically focusing the fluid in the second planar direction to further focus the particles.

The present invention further includes methods for dislodging bubbles in a fluidic system. These methods comprise providing a fluid stream through a channel and resonating the channel at an acoustic frequency. These methods also include providing a fluid stream through a channel and vibrating the channel walls at a low frequency.

An embodiment of the present invention is an apparatus that acoustically focuses particles into a quasi-planar arrangement in a fluid. This embodiment preferably comprises a capillary with an oblate cross-sectional geometry and at least one transducer coupled to the capillary. The capillary is preferably elliptical. This embodiment can further comprise an imager for imaging the particles.

Another embodiment of the present invention comprises a method for acoustically focusing particles into a quasi-planar arrangement in a fluid comprising particles. The method preferably comprises flowing the fluid comprising particles therein through a flow chamber comprising an oblate cross-sectional geometry and subjecting the fluid to acoustic radiation pressure. The cross-sectional geometry of the flow chamber is preferably elliptical. This embodiment can also include imaging the particles.

Objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings:

FIGS. 6A and 6B illustrate focused particle stream flowing through an elliptical cross section line driven capillary according to one embodiment of the present invention;

DETAILED DESCRIPTION OF THE INVENTION

As used herein "a" means one or more.

As used herein "flow chamber" means a channel or capillary having a shape selected from rectangular, square, elliptical, oblate circular, round, octagonal, heptagonal, hexagonal, pentagonal, and trigonal. It is not necessary for the shape of the interior walls of the flow chamber to be the same as the shape of the exterior walls. As a non-limiting example, a flow chamber can have an interior wall defined by a circular shape and the exterior wall defined by a rectangular shape. Additionally, the flow chamber can be part of a composite construction of materials and geometries wherein one of the above shapes defines the interior shape of the flow chamber.

As used herein "capillary" means a channel or chamber having a shape selected from rectangular, square, elliptical, oblate circular, round, octagonal, heptagonal, hexagonal, pentagonal, and trigonal. It is not necessary for the shape of the interior walls of the capillary to be the same as the shape of the exterior walls. As a non-limiting example, a capillary can have an interior wall defined by a circular shape and the exterior wall defined by a rectangular shape.

One aspect of one embodiment of the present invention provides for ease in alignment during device fabrication and for larger acoustic source apertures. Another aspect of one embodiment of the present invention provides for a line-driven capillary with oblate cross-section to obtain quasi-planar particle concentration. Another aspect provides for planar particle concentration without particles contacting and/or staying in contact with the inner capillary wall. Another aspect provides for imaging applications where particles spread over a plane in a narrow depth of field. Another aspect provides for applying acoustic radiation pressure forces to assist in stabilizing standard hydrodynamic particle focusing systems. Yet another aspect provides for reduced sheath consumption in slow-flow hydrodynamic systems and to assist in particle focusing in planar systems (e.g. chip based systems). Still another aspect provides a method to dislodge bubbles from fluidic systems.

Construction of Line-Driven Capillaries with Grooved Source

Figure 1:
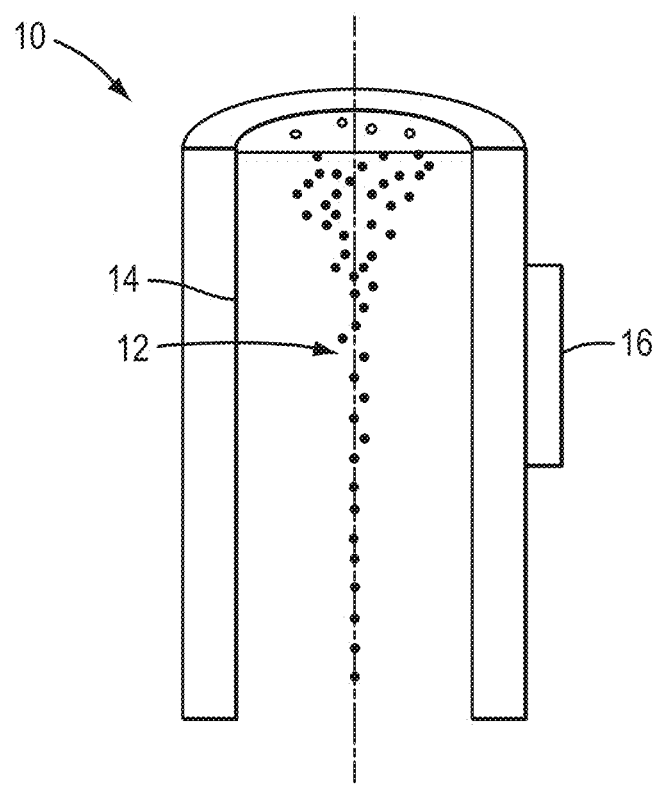
FIG. 1 is an embodiment of the present invention illustrating a line drive capillary where particles are acoustically focused to the central axis of the capillary.

Line-driven capillaries are used to acoustically concentrate particles in a flowing stream within a capillary. Particles experience a time-averaged acoustic force resulting from acoustic radiation pressure. FIG. 1 illustrates line-driven capillary 10 operating in a dipole mode where particles 12 are acoustically focused to the central axis of capillary 14 to the position of an acoustically formed particle trap according to one embodiment of the present invention. (The embodiment illustrated in FIG. 1 is applicable to any vibrational mode of the system whether it be monopole, dipole, quadrapole, etc., or a combination of modes.) It is possible to drive different mode configurations with different spatial configurations of sources attached to the capillary.

Another aspect of one embodiment of the present invention provides a line-driven capillary system that both delivers stable acoustic signals within the capillary and possess consistent, repeatable electrical properties of the electromechanical circuit that drives the system.

In one embodiment of the present invention, line-driven capillary 10 is comprised of capillary 14 coupled to vibration source 16. Capillary 14 can be made from, but are not limited to glass, metal, plastic, or any combination thereof. Low loss materials are preferably particle concentrators and stainless steel is one of the better capillary materials. Vibration source 16 is preferably comprised of a piezoelectric material. Examples of piezoelectric materials include but are not limited to PZT, lithium niobate, quartz, and combinations thereof. Vibration source 16 can also be a vibration generator such as a Langevin transducer or any other material or device that is capable of generating a vibration or surface displacement of the capillary. Another aspect of the embodiment of the present invention comprises an acoustically focused line drive capillary that yields a larger acoustic source aperture than a standard line contact.

Figure 2:
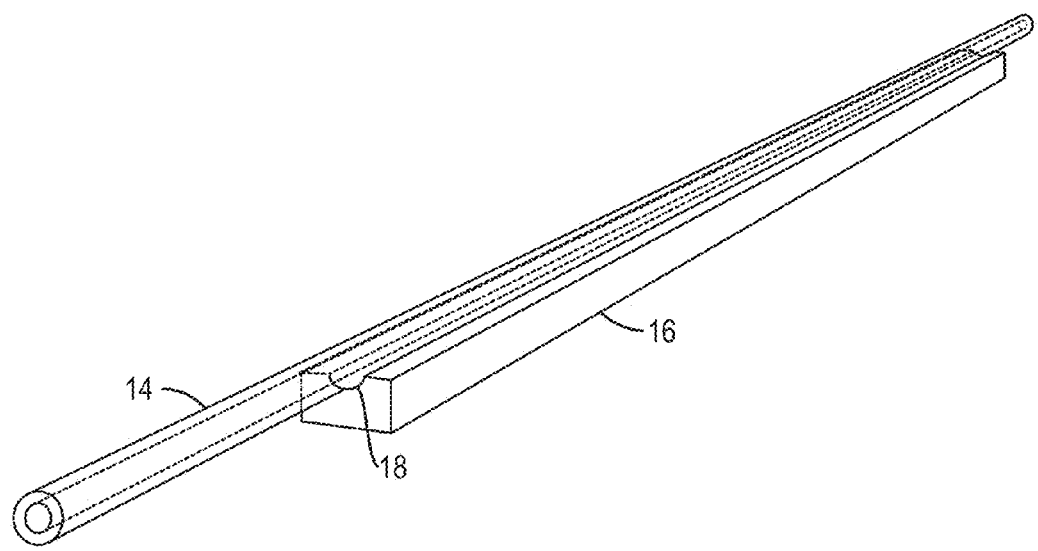
FIG. 2 illustrates construction of line-drive capillary with grooved piezoelectric transducer (PZT) according to one embodiment of the present invention.

According to one embodiment of the present invention, groove 18 is machined into vibration source 16 into which capillary 14 is cradled, as illustrated in FIG. 2. A diagram is shown in FIG. 2, which comprises line-drive capillary 10 with grooved vibration source 16, a small PZT slab with machined circular groove 18 is adhered to capillary 14 to improve manufacturability and acoustic performance. Groove 18 is circular with a radius that matches the outer radius of capillary 14 plus a small glue layer. The number of grooved vibration sources attached to capillary 14 is not limited to one. Using more than one grooved vibration source is advantageous in driving different acoustic modes that require specific spatial dependence. For example, a dipole mode is driven with a single source or with two sources attached to opposite walls of capillary 14 and driven 180 degrees out of phase. A quadrapole mode is driven by attaching sources at orthogonal positions (90 degree offset from one another) and driven out of phase. For capillaries of non-circular cross section, groove 18 will typically take on the cross sectional geometry of capillary 14. For example, an elliptical cross section capillary would require an elliptical cross section groove. Capillary 14 is preferably held to vibration source 16 with a small glue layer. When using a piezoelectric crystal as vibration source 16, it is not necessary to have an electrical conducting layer inside groove 18 that is cut into the crystal. Construction with and without conductors in groove 18 have been demonstrated.

Another aspect of one embodiment of the present invention provides ease of device construction.

Yet another aspect of one embodiment of the present invention provides for larger acoustic source aperture as compared to a true line-driven device.

Still another aspect of one embodiment of the present invention provides for repeatable acoustic/electrical performance.

Another aspect of one embodiment of the present invention provides for ease in alignment of capillary 14 with vibration source 16.

Still another aspect of one embodiment of the present invention provides for a larger glue surface upon which to attach a transducer.

Additionally, it is not necessary for the capillary to have a circular cross section. In one embodiment of the present invention, a square cross section groove in PZT is used. Capillaries can be constructed with many geometries including but not limited to elliptical, square, rectangular, general oblate shapes, as well as any cross sectional geometry.

Quasi-Planar Focusing of Particles in Line-Driven Oblate Capillaries

Figure 3:
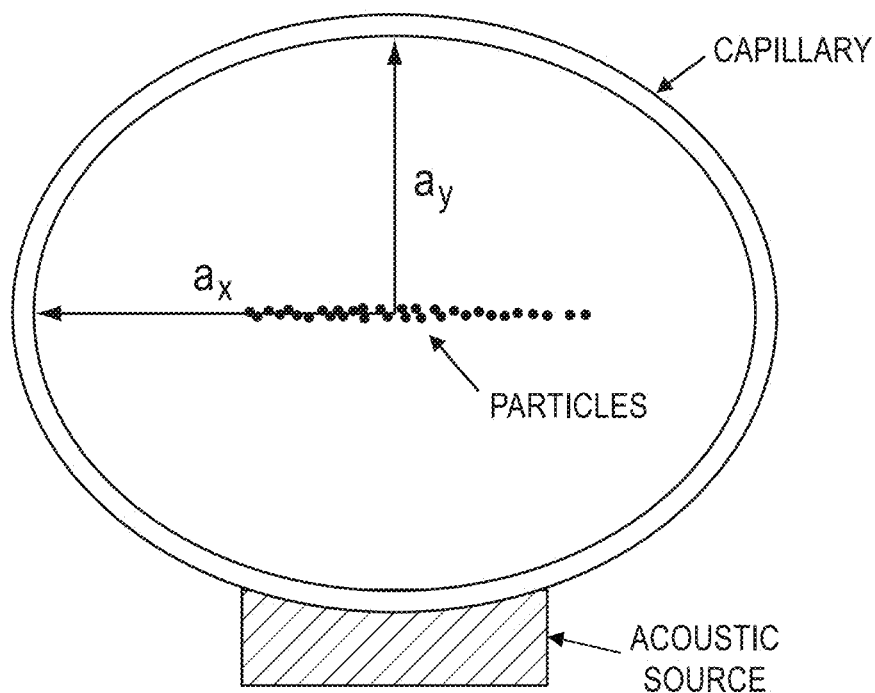
FIG. 3 illustrates a diagram of a line driven capillary with an elliptical cross section according to one embodiment of the present invention.

Referring now to FIG. 3, line-driven capillaries with circular cross sections can be driven to align particles along the axis of the cylindrical capillary when driven in a dipole mode in one embodiment of the present invention. In this embodiment, it may be desirable in certain applications to localize the particles only to a specific plane within a capillary, not to a point or line. This is the case for imaging applications where particles need to be distributed in a plane within a narrow depth of field of the imaging optics. A method to spatially distribute the particles is to break the circular symmetry of the system. By making the cross section of the capillary more oblate (e.g. elliptical), it is possible to keep tight spatial localization in one dimension while allowing the particles to be spatially distributed in another dimension. This method is advantageous for systems requiring particles placed in a planar (or quasi-planar) arrangement.

For example, an acoustically driven capillary with an elliptical cross section is illustrated in FIG. 3. In this embodiment, acoustic force spatially distributes particles in a plane along the major axis and tightly confines particles along the minor axis. The aspect ratio A of the ellipse is given by the ratio of the minor axis ay to major axis ax: A=ay/ax. To calculate the acoustic force on particles within the capillary, the acoustic radiation pressure force on a compressible, spherical particle of volume V in an arbitrary acoustic field can be written in terms of an acoustic radiation pressure force potential U (Gor'kov 1962):

$$U = \frac{4}{8}\pi a^3 \left[ \left( \beta_o \frac{\langle p^2 \rangle}{2} \right) f_1 - \frac{3}{2} \left( \frac{\rho_o \langle v^2 \rangle}{2} \right) f_2 \right]$$

Here, a is the particle radius, $\beta_0$ is the compressibility of the surrounding fluid, and $\rho_0$ is the density of the surrounding fluid. The pressure and velocity of the acoustic field in the absence of the particle are described by p and v, respectively, and the brackets correspond to a time-averaged quantity. The terms $f_1$ and $f_2$ are the contrast terms that determine how the mechanical properties of the particle differ from the background medium. They are given by:

$$f_1 = 1 - \frac{\beta_p}{\beta_o}$$

$$f_2 = \frac{2(\rho_p - \rho_o)}{(2\mu_p - \mu_o)}$$

The subscript p corresponds to intrinsic properties of the particle. The force F acting on a particle is related to the gradient of the force potential by:

$$F = -\nabla U$$

Particles are localized at positions where the potential U displays a minimum. (For a circular cross section capillary, a potential minimum is coincident with the axis of the capillary forming the particle trap in FIG. 1.)

Figure 4:
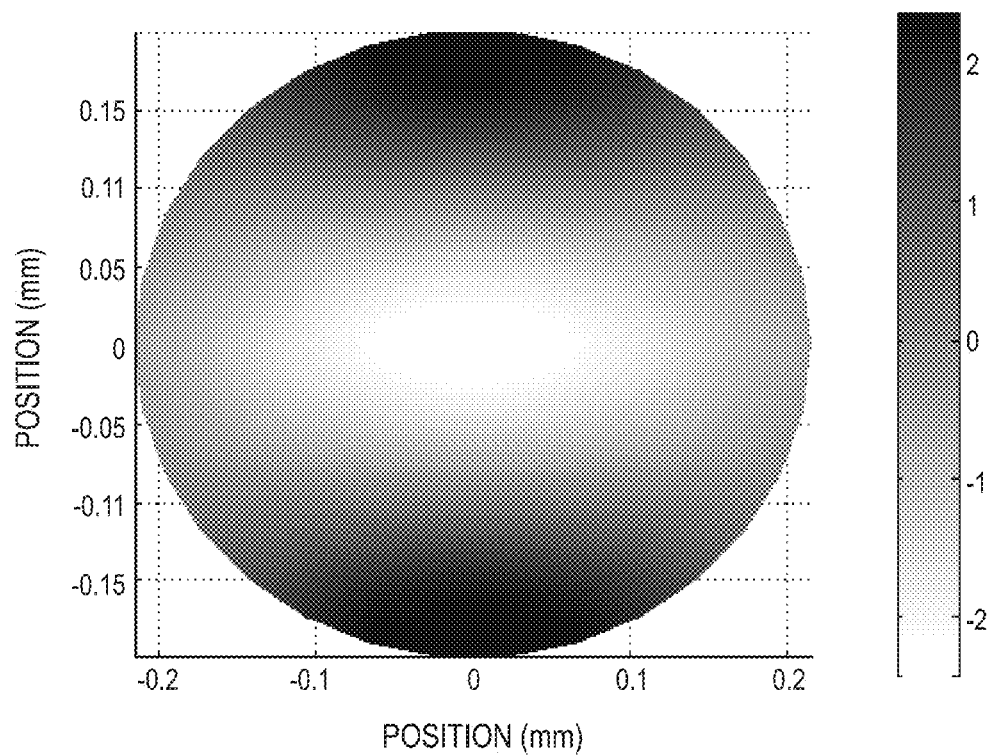
FIG. 4 illustrate force potential U in a line-driven capillary with elliptical cross section according to one embodiment of the present invention.

The force potential U for an elliptical cross section capillary line-driven in a dipole type mode is illustrated in FIG. 4. The potential is calculated for latex spheres in water. In this configuration, the particles experience a force that transports them to a potential well that appears to stretch between the foci of the ellipse. The particles are also more tightly focused in the direction of the minor axis and are more "spread out" in the direction of the major axis.

Figure 5:
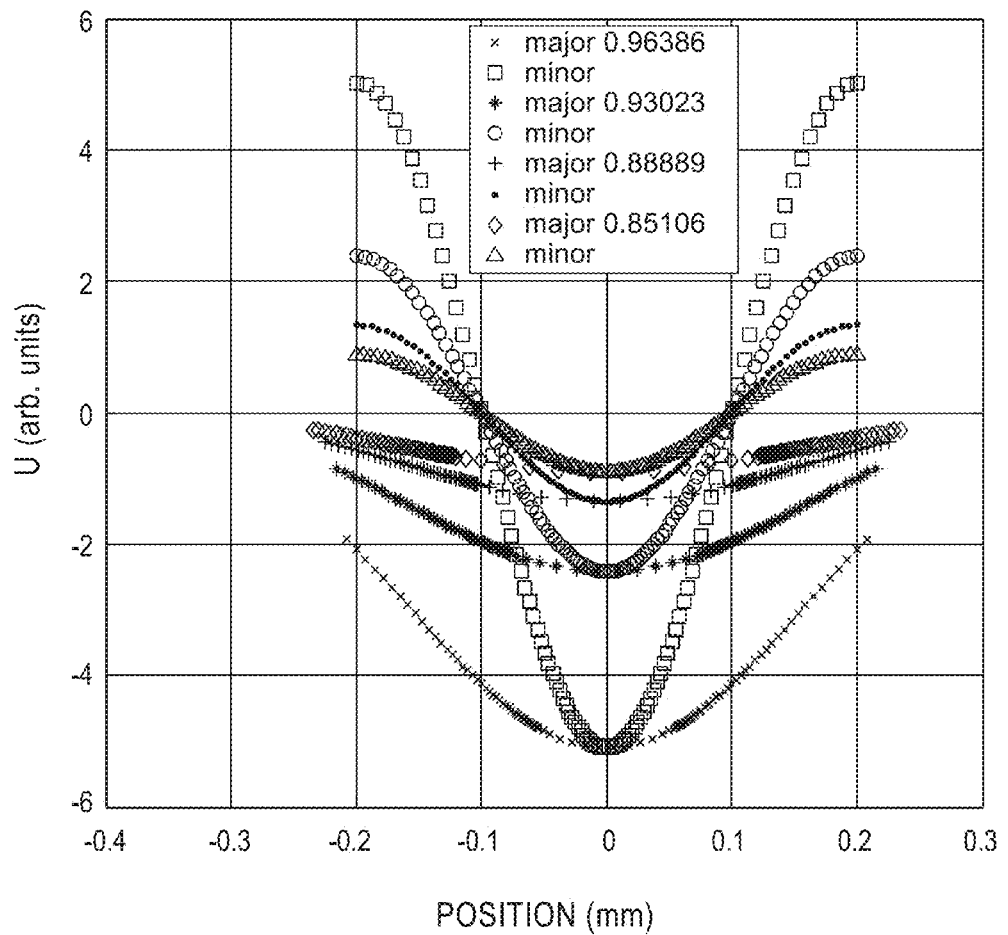
FIG. 5 illustrate force potential for different aspect ratios for a spherical latex particle in an elliptical cross section, line-driven capillary according to one embodiment of the present invention.

Depending upon the aspect ratio of the ellipse, the force potential in orthogonal directions can be dramatically different. This is illustrated in FIG. 5. In FIG. 5, force potential for different aspect ratios for a spherical latex particle in an elliptical cross section, line driven capillary is shown. For this configuration, the particles are more localized along the minor axis and less localized along the major axis. A change in frequency can cause greater localization along the major axis and less localization along the minor axis. For aspect ratios closer to unity, the potential well is more pronounced than for aspect ratios further from unity. Note the gradient of the potential is smaller in the direction of the major axis. The reduced gradient implies less localization of the particles along this direction. As the aspect ratio of the ellipse decreases, the potential well depth decreases resulting in milder gradients and less localization. Therefore, with decreasing aspect ratio, particles experience a greater spread along the major axis of the ellipse (reduced force due to reduced gradient). (There is also a spreading of particles along the minor axis, but to much less of an extent than in the direction of the major axis.)

Results showing this effect are given in FIG. 6. FIG. 6(a) displays an example of particles flowing through an elliptic cross section capillary. In this example, the particles are approximately 5.6 mm diameter fluorescent latex spheres (more specifically, polystyrene beads) and appear as horizontal streaks in the image. Flow is from left to right. The image plane contains the major axis of the ellipse and the central axis of the capillary. The particles are spread across approximately half the width of the capillary forming a ribbon of particles. In this example, there is enough force on the particles directed toward the axis of the capillary to keep them off the walls. In FIG. 6(b), the image plane has been rotated 90 degrees to include the minor axis of the ellipse and the central axis of the capillary. In this direction, the gradient along the potential well is greater leading to a greater confinement of the particles along the capillary axis. Here they are confined to a single line coincident with the central axis of the capillary.

Several characteristics of these types of modes exist:

Particles can be tightly focused either along major or minor axis of ellipse with 'loose' focusing along the orthogonal direction (selection of which axis is the weak focusing direction is mode dependent).

In the weakly focused dimension, enough force can exist to keep particles off the wall of the device.

Particles are confined to a plane which is conducive to imaging applications where it is necessary to place particles in a common plane especially when depth of focus is small.

Acoustically Assisted Hydrodynamic Focusing of Particles

Figure 7A:
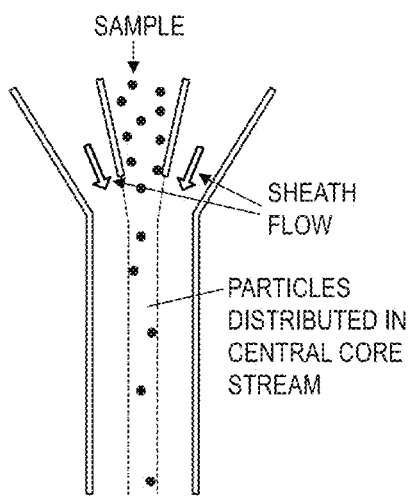
FIGS. 7A and 7B illustrates hydrodynamically focused particles distributed in a central core stream according to one embodiment of the present invention.

Hydrodynamically-focused particle streams are used in flow cytometry as well as other areas where precisely aligned particles in a flowing core stream are required. Hydrodynamic focusing is traditionally employed in flow cytometry to focus particles into a tight stream for laser interrogation. A diagram of a hydrodynamically focused particle stream is illustrated in FIG. 7(a). In this example, a sample is injected into a central core stream contained within a coaxial sheath flow. The sheath fluid is typically a clean buffer solution traveling at many times the velocity of the sample input in order to hydrodynamically confine the central sample stream into a smaller cross sectional area. This action confines the particles in a cylindrical core stream of very narrow width. The hydrodynamically focused core stream radius r is given approximately as $$r = \sqrt{\frac{Q}{\pi v}}$$

where Q is the volumetric flow rate of the core stream and v is the velocity of the core stream. Note that larger volumetric sample delivery and/or lower velocities yield larger diameters of the core stream.

Hydrodynamically focused sample streams can suffer from instabilities of the central core stream position as a function of many factors. These can include but are not limited to nucleation of bubbles on the cell walls that alter stream lines, turbulence, and combinations thereof. It is advantageous to assist hydrodynamically focused systems with an external force that stabilizes the spatial position of the central core stream. An embodiment of the present invention comprises a device that uses multiple fluidic streams to steer the central core stream.

Figure 7B:
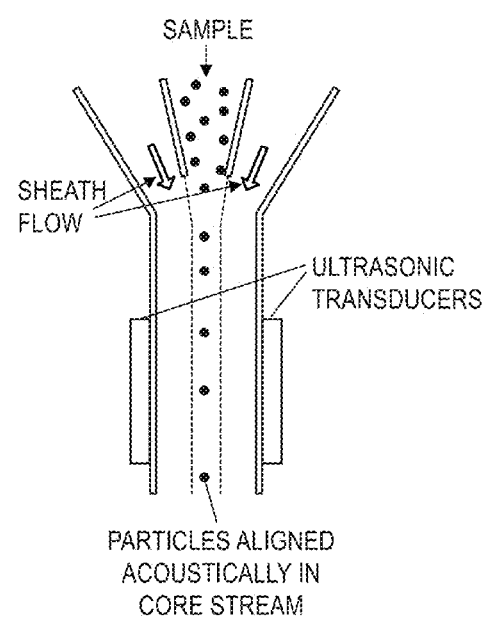

FIG. 7(b) illustrates an embodiment of the present invention comprising an acoustically assisted hydrodynamically focused sample stream. In FIG. 7(b), an outer coaxial flow of sheath fluid confines the central core stream containing the sample. By applying acoustic forces to the particles in the hydrodynamically focused core stream, the particles are preferably focused further within the stream.

One embodiment of the present invention combines acoustic focusing of particles with hydrodynamic focusing. Acoustic focusing assists hydrodynamic focusing systems by stabilizing the absolute location of the particle stream against external forces. Acoustic focusing is also used to further tighten the focus of the particle stream within a hydrodynamically focused system where reduction in sheath fluid consumption or increase in sample throughput is desired without the loss of particle focus quality within the stream. This is particularly important for applications where the sample is dilute. A prime example is high speed sorting of "sticky" cells that must be kept at lower concentration to prevent aggregation. Another example is where reduction of sheath fluid is a priority without sacrificing particle focus. Furthermore, some systems that employ acoustic focusing may not want the sample to contact the walls. (For example, this will keep the build-up of proteins and small particles that are unaffected by acoustic radiation pressure off the capillary walls. These systems can use a slow, low-volume sheath to entrain the sample. Acoustic focusing can then be used to tightly focus the particles within the sample stream.)

An example of acoustically assisted hydrodynamic focusing is shown in FIG. 7(b). In this example, a standard hydrodynamically-focused system is outfitted with ultrasonic transducers to set up a standing wave in the fluid cavity. The particles are initially hydrodynamically focused. Ultrasonic radiation pressure then forces the particles to a force potential minimum located along the axis of the central core stream where they are further aligned within the central core stream.

Figure 8:
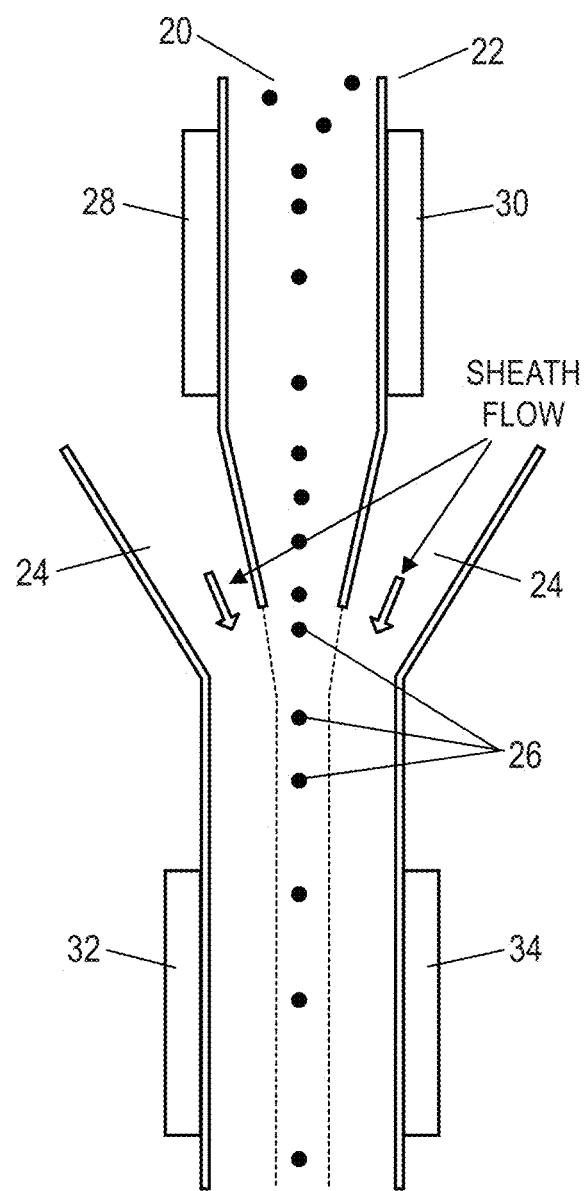
FIG. 8 illustrates acoustic focusing of particles in combination with hydrodynamic focusing according to one embodiment of the present invention.

Referring now to FIG. 8, a schematic of a device capable of applying acoustic focusing prior to, during, or both prior to and during hydrodynamic focus as illustrated according to one embodiment of the present invention. This embodiment comprises sample 20 flowing through capillary 22. Sheath fluid 24 hydrodynamically focusing particles 26. Transducers 28 and 30 acoustically focus particles 26 along the axis of the central core prior to hydrodynamic focusing while transducers 32 and 34 acoustically focus particles 26 during hydrodynamically focusing.

Figure 9A:
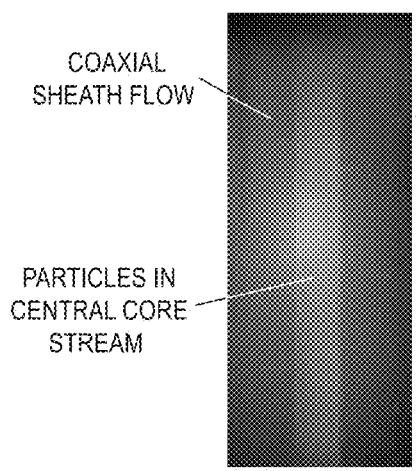
FIGS. 9A and 9B illustrates acoustically assisted hydrodynamic focusing according to one embodiment of the present invention.
Figure 9B:
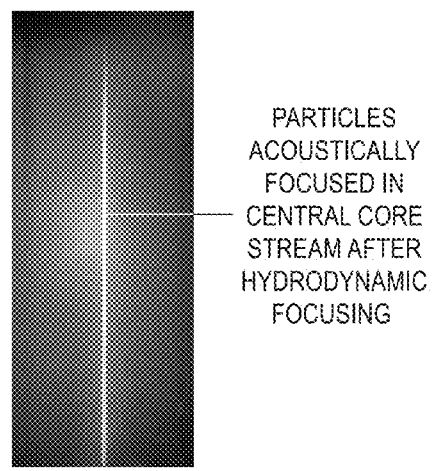

Measurements demonstrating acoustically assisted hydrodynamic focusing are illustrated in FIGS. 9A and 9B. FIG. 9A demonstrates hydrodynamic focusing in a cylindrical channel of width 500 microns. The central core stream comprises approximately 5.6 μm diameter polystyrene particles in solution (approx. 0.0025% by volume). The central core stream is surrounded by a coaxial sheath flow that contains a phosphate buffer solution. FIG. 9B shows particles in the central core stream during hydrodynamic focusing. The sheath fluid is introduced at a volumetric flow rate of between approximately 100 to 1,000 microL/min and preferably at a rate of approximately 400 microL/min, and the sample core stream is introduced at a volumetric flow rate of between 50 to 500 microL/min and preferably at a rate of approximately 100 microL/min. The frequency of the acoustic excitation is 2.1 MHz. In the image on the right, an acoustic field is activated that is designed to produce a particle trap along the axis of the core sample stream. Particles within the core sample stream are further isolated within the core stream by the acoustic field.

Aspects of acoustically assisting hydrodynamically focused sample streams include but are not limited to:
Repeatable location of focused particle stream
Increased particle focusing in lower velocity hydrodynamically focused streams thereby reducing the sheath fluid requirements (particles spatially confined to a stream smaller in diameter than core stream)
Increased sample throughput of dilute samples while maintaining tight spatial positioning
Less effect of turbulence and other exterior influences on the exact location of the focused particles
Method to isolate sample stream from capillary walls in a system where predominant particle focusing is conducted by acoustic radiation pressure (e.g. line-driven capillary)

There are many different arrangements where both acoustically focusing and hydrodynamically focusing can be advantageous. FIG. 7(b) displays a device with two transducers attached to a hydrodynamic focusing cell. The acoustic field can be used in a cell that is circular, square, or any other geometry. The number of transducers shown in FIG. 7(b) is two. The minimum number of transducers is one. Using more than one transducer provides feedback to monitor the acoustic field within the chamber. Additionally transducers may be attached in orthogonal directions to create force fields that are optimized for a given application. In an embodiment of the present invention, it is advantageous to focus the particles single file into a line within the core sample stream. In another embodiment of the present invention, it is advantageous to focus particles in one dimension and allow them to spread out in an orthogonal direction.

Figure 10:
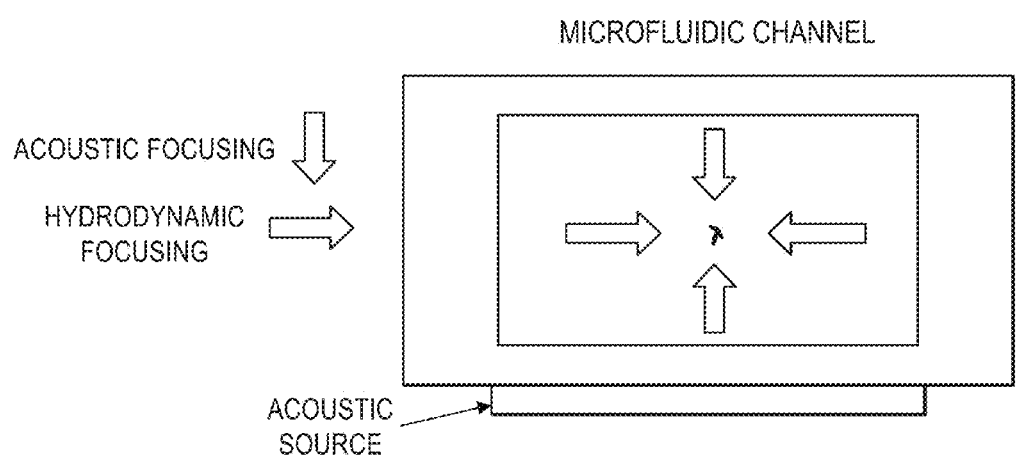
FIG. 10 illustrates a combination of acoustic and hydrodynamic focusing in a microfluidic channel according to one embodiment of the present invention.

The ability to use acoustically assisted hydrodynamic focusing of particles is also advantageous for applications in microfluidics. Hydrodynamic focused particle streams in microchannels, microfluidic chips, or other rectangular (or quasi-rectangular) channel geometries can be enhanced by combining acoustic focusing and hydrodynamic focusing. In one embodiment of the present invention and to reduce sheath fluid consumption, one dimensional hydrodynamic focusing can be used, as illustrated in FIG. 10. A combination acoustic and hydrodynamic focusing in a microfluidic channel is shown. Hydrodynamic focusing localizes particles in the horizontal direction and acoustic focusing localizes particles in the vertical direction. Ease of implementation for both acoustic and hydrodynamic focusing in planar devices is accomplished in this embodiment. (This can also work if the force diagram in FIG. 10 is rotated 90 degrees.) Using both acoustic focusing and hydrodynamic focusing also keeps small particles and molecular species from contacting the channel walls.

Another embodiment of the present invention allows for serial acoustic focusing in microfluidic applications. Acoustic focusing applied to a flowing stream of particles in a quasi-rectangular cross section chamber focuses particles into a ribbon-like structure. In order to preserve the layered construction used in many microfluidic assemblies, it is advantageous to preserve the placement of the transducers in parallel planes. Thus, a method to focus particles into a narrow spatial configuration involves acoustically focusing particles into a plane, rotating the flow by 90 degrees, and then acoustically focusing again into the new orthogonal plane. The net result is a narrow spatial distribution of particles. When the transducer is used to excite a dipole type mode within the flow chamber, the result is particles narrowly focused about the central axis of the flow chamber.

Bubble Dislodging from Fluidic Systems

In traditional flow cytometry, bubbles that adhere to walls of a fluidic system are problematic. They can interfere by moving laminar flow lines, affecting local reactions, deviating focused particle streams. For example, in flow cytometers, bubbles in a fluidic system can have the effect of moving the position of the hydrodynamically-focused sample stream. This movement appears as a misalignment of the optical system to the user and a recalibration is required. A technique to dislodge bubbles from nucleation sites in fluidic systems, especially microfluidic systems, is very desirable.

Acoustic radiation pressure has been shown to have a large effect on bubbles in fluids due to the large mismatch in density and compressibility between liquids and gases. Acoustic energy can be used to dislodge bubbles from fluidic system in several different ways.

In one embodiment of the present invention, a fluidic system is engineered such that when resonated at an appropriate acoustic frequency, bubbles experience a force that pulls them away from the wall and stabilizes their equilibrium position within the fluid stream that exists at the location of a pressure node (for bubbles driven at frequencies below their monopole resonance). The chamber is preferably driven acoustically with either an internal acoustic source or noninvasively with a source attached to an outer wall of the chamber. This is a robust method to dislodge bubbles from walls.

In another embodiment of the present invention, vibration of the channel walls at low frequencies is preferably used to dislodge the bubbles. By vibrating the wall as part of a structural resonance of the system, large surface displacements are achieved. (These displacements are typically larger at lower frequencies.) Large forces coupled with large displacements are preferably used to break the bond between the bubble and the chamber surface. The inertial forces coupled with localized fluid flows at the chamber wall surface are effective at bubble dislodgement.

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above and/or in the attachments, and of the corresponding application(s) are hereby incorporated by reference.

What is claimed is:

1. A system for acoustically concentrating particles comprising:
    a capillary, wherein the capillary has an elliptical cross-section and an outer wall, wherein the capillary is configured to flow particles in a stream; and
    a single vibration source, including a groove, configured to acoustically focus a plurality of particles to a plane within the capillary, wherein the capillary is coupled to the vibration source, and wherein the groove is contoured to the shape of the outer wall of the capillary.

2. The acoustic focusing capillary of claim 1 wherein said capillary is coupled to said vibration source at said groove.

3. The acoustic focusing capillary of claim 1 wherein said groove has an approximately same cross-sectional geometry as said capillary.

4. The acoustic focusing capillary of claim 1 wherein said capillary is oblate.

5. The acoustic focusing capillary of claim 1 wherein said vibration source comprises a piezoelectric material.

6. The acoustic focusing capillary of claim 1 where said groove increases an acoustic source aperture of said capillary.

* * * * *